United States Patent [19]

Jensen et al.

[11] Patent Number: 5,034,315
[45] Date of Patent: Jul. 23, 1991

[54] **OLIGONUCLEOTIDE PROBES COMPLEMENTARY TO AND METHODS FOR DISTINGUISHING *TREPONEMA HYODYSENTERIAE* RNA SEQUENCES**

[75] Inventors: Neil S. Jensen; Thaddeus B. Stanton; Thomas A. Casey, all of Ames, Iowa

[73] Assignee: The United States of America, as represented by the Secretary of Agriculture, Washington, D.C.

[21] Appl. No.: 496,579

[22] Filed: Mar. 21, 1990

[51] Int. Cl.$^5$ .............. C12Q 1/68; C12Q 1/02; C01N 33/566; C07H 19/06

[52] U.S. Cl. .................. 435/6; 435/29; 435/34; 436/501; 935/77; 935/78; 536/26; 536/27; 536/28

[58] Field of Search ............. 536/26, 27, 28; 435/6, 435/29, 34; 436/501, 94; 935/77, 78

[56] References Cited

PUBLICATIONS

Joens et al., The Diagnosis of Swine Dysentery Using a Labeled Nucleic Acid Probe., Proc. Intl. Ag. vol. Soc. 10th Cong., Rio de Janiero, Brazil, 1988.
Neil S. Jensen et al., "Detection of *Treponema Hyodysenteriae*, the Agent of Swine Dysentery. . ." Abstr. D-234, Abstracts of 89th Ann. Mtg. of American Society ofr Microbiology, New Orleans, LA, 5/14–18/89.
Ulf B. Göbel et al., "Oligonucleotide Probes Complementary to Variable Regions of Ribosomal RNA Discriminate Between Mycoplasma Species", J. Gen. Microbiol. 133: 1969–1974 (1987).
G. Haun et al., "Oligonucleotide Probes for Genus-, Species- and Subspecies-Specific Identification of Representatives of the Genus Proteus," FEMS Microbiol. Lett. 43: 187–193 (1987).

*Primary Examiner*—Robert A. Wax
*Assistant Examiner*—Stephanie W. Zitomer
*Attorney, Agent, or Firm*—M. Howard Silverstein; John D. Fado; Curtis P. Ribando

[57] ABSTRACT

Single-stranded oligonucleotide probes complementary to a signature region of *Treponema hyodysenteriae* (*T. hyo*) 16S rRNA are useful in distinguishing this pathogenic species of Treponema from closely related, non-pathogenic species. The probes find practical application in diagnosing swine dysentary from clinical samples, such as fecal material. They are also useful in differentiating *T. hyo* strains based on RFLP analysis.

18 Claims, No Drawings

OLIGONUCLEOTIDE PROBES COMPLEMENTARY TO AND METHODS FOR DISTINGUISHING *TREPONEMA HYODYSENTERIAE* RNA SEQUENCES

BACKGROUND OF THE INVENTION

1. Field of the Invention

*Treponema hyodysenteriae* (*T. hyo*) is an anaerobic spirochete that causes swine dysentery [D. J. Taylor et al., Br. Vet. J. 127: lviii–lxi (1971); D. L. Harris et al., Vet. Med./Small Anim. Clin. 67: 61-64 (1972)], a severe, mucohemorrhagic intestinal disease of economic importance to the U.S. pork industry [anonymous, "Research and Education Priorities," National Pork Producers Council, Des Moines, IA (1984)]. In addition, swine dysentery has been reported in every major pig-producing country [R. A. Roncalli et al., "Geographic Distribution of Swine Dysentery," In Proceedings of the 4th International Congress of the Pig Veterinary Society, L. 17 (1976)].

Effective diagnosis of this disease is currently hindered by the time needed to culture *T. hyo* from fecal specimens (4–6 days), and the difficulty in distinguishing *T. hyo* from nonpathogenic spirochetes such as *T. innocens* and *T. succinifaciens*, that also inhabit the swine intestine. This invention relates to a diagnostic tool useful in a rapid and accurate assay for the presence of *T. hyo* in biological samples taken from swine.

2. Description of the Prior Art

Various methods have been used in the diagnosis of swine dysentery. These methods include examination of samples by microscopy and direct or indirect immunofluorescence [D. Hunter et al., Vet. Rec. 101: 303-304 (1977); C. N. Saunders et al., Vet. Rec. 94: 491-492 (1974)]. Serological methods include a passive hemolysis test [E. M. Jenkins et al., Inf. Imm. 14: 1106-1108 (1976)], microtitration agglutination test [L. A. Joens et al., J. Clin. Microbiol. 8: 293-298 (1978)], and ELISA [L. A. Joens et al., J. Clin. Microbiol. 15: 249-252 (1982); I. T. Egan et al., Am. J. Vet. Res. 44: 1323-1328 (1983)], which are all designed to detect an immune response against *T. hyo* in infected pigs.

The most widely used method for diagnosing swine dysentery is by streaking a fecal specimen on a blood agar plate containing the antibiotic spectinomycin [Songer et al., J. Clin. Microbiol. 4: 57-60 (1976)], and examining the plate for the presence of β-hemolytic zones following 4-6 days incubation at 39° C. under anaerobic conditions. However, the long incubation times required and a lack of sensitivity and specificity make this test inadequate.

Nucleic acid probes are a sensitive and rapid alternative to culture methods for the detection of pathogens [L. Palmer et al., "Selection of DNA Probes for Use in the Diagnosis of Infectious Disease," In Rapid Detection and Identification of Infectious Agents, D. T. Kingsbury and S. Falkow, eds., Academic Press, Orlando, FL, pages 211-218 (1985); F. C. Tenover, Clin. Microbiol. Rev. 1: 82-101 (1988)], particularly in the case of fastidious or noncultivatable organisms. DNA probes, for example, are now in common usage and can be custom designed in terms of their sizes and specificities for a variety of prospective applications. The sizes of these probes can range from entire plasmids (kilobases in size) down to simple 10- to 15-base synthesized oligonucleotides. DNA probes can be tailored to bind to different nucleic acids including DNA, ribosomal RNA (rRNA), and messenger RNA (mRNA). A given probe will bind to specific nucleotide sequences. A radioactive, enzymatic, or organic label bound to the probe allows it to be detected.

DNA probes to *Campylobacter pylori* [B. L. Wetherall et al., J. Med. Microbiol. 26: 257-263 (1988)], Mycobacteria sp. [P. D. Ellner et al., J. Clin. Microbiol. 26: 1349-1352 (1988)], and *Pseudomonas fluorescens* [H. Festl et al., Appl. Environ. Microbiol. 52: 1190-1194 (1986)] as well as other pathogens have been successfully developed.

DNA probes specific for rRNA sequences have been used successfully in the detection of Mycoplasma sp. [U. B. Göbel et al., J. Gen. Microbiol. 133: 1969-1974 (1987)], Proteus sp. [G. Haun et al., FEMS Microbiol. Lett. 43: 187-193 (1987)], and Bacterioides sp., Acinobacillus sp., and Haemophilus sp. [P. L. Chuba et al., J. Gen. Microbiol. 134: 1931-1938 (1988)]. No cross hybridization to closely related strains occurred and a detection limit of less than $5 \times 10^3$ cells was found. Various diagnostic kits based on DNA probes are now available for use in clinical labs and undoubtedly more will follow.

DNA probes can also be used in the detection of sequence variation in the DNA of related organisms by restriction fragment length polymorphism (RFLP) analysis. When a sample of DNA is cut with a restriction endonuclease, the size of the DNA fragments generated can vary depending on the sequence variation in the DNA samples examined. Different restriction endonucleases enable the detection of different polymorphisms.

To analyze the variety of fragment sizes from different samples, the digested DNA is electrophoresed in an agarose gel to separate the fragments based on size. The gel is then stained with ethidium bromide and RFLPs are visually identified, or the fragments are transferred from the gel to a solid support and hybridized with a DNA probe which binds to the polymorphic fragment(s) of interest. The sensitivity and specificity of this technique depends on the restriction endonucleases and DNA probes used.

RFLP analysis is already being used in classifying bacteria [S. E. Douglas et al., Appl. Environ. Microbiol. 54: 3071-3078 (1988)] and amoebae [G. L. McLaughlin et al., J. Clin. Microbiol. 26: 1655-1658 (1988)], for agricultural genetics [J. S. Beckman, Bio/technology 6: 1061-1064 (1988)], and for DNA fingerprinting in human genetics [R. Schafer et al., Electrophoresis 9: 369-374 (1988)].

SUMMARY OF THE INVENTION

We have taken advantage of a unique base sequence we found in a region of the 16S rRNA in *T. hyo* which allows the rRNA of *T. hyo* to be distinguished from other treponemes. An oligonucleotide probe complementary to that unique sequence has been constructed and is useful in detecting *T. hyo* rRNA target sequences by hybridization with clinical samples obtained from swine. The probe can also be used to differentiate *T. hyo* strains based on RFLP analysis.

In accordance with this discovery, it is an object of the invention to provide a rapid and effective alternative to bacteriological culture for diagnosis of swine dysentery.

It is also an object of the invention to provide an oligonucleotide probe useful for clinical diagnosis of swine dysentery that is characterized by a high degree of specificity and selectivity for *T. hyo*.

More specifically, it is an object of the invention to identify infected swine, including those which are asymptomatic and shedding *T. hyo* in their feces.

In conjunction with detecting *T. hyo* in individual animals, it is an object of the invention to enable monitoring the spread of swine dysentery throughout a herd.

Another object of the invention is to provide a tool for identifying different strains of *T. hyo*.

A further object of the invention is to provide a diagnostic basis for designing an effective control program for swine dysentery on pig farms.

Other objects and advantages of this invention will become readily apparent from the ensuing description.

GLOSSARY

For purposes of this invention, the following standard abbreviations and terms used herein have been defined below. Also included are a listing of biological materials and reagents mentioned in the specification.

ABBREVIATIONS

AT$^{32}$P = $^{32}$P-labelled adenosine triphosphate
bp = base pairs
DNA = deoxyribonucleic acid
EDTA = ethylenediaminetetraacetic acid
RFLP = restriction fragment length polymorphism
RNA = ribonucleic acid
mRNA = messenger ribonucleic acid
rRNA = ribosomal ribonucleic acid
ss-rRNA = single-stranded ribosomal ribonucleic acid
SDS = sodium dodecyl sulfate

TERMS

DNA or RNA sequence: a linear series of nucleotides connected one to the other by phosphodiester bonds between the 3' and 5' carbons of adjacent pentoses.

hybridization: the pairing together or annealing of complementary single-stranded regions of nucleic acids to form double-stranded molecules.

oligonucleotide: a linear series of 2-100 deoxyribonucleotides or ribonucleotides connected one to the other by phosphodiester bonds between the 3' and 5' carbons of adjacent pentoses.

nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("U").

oligonucleotide probe: a single-stranded piece of DNA or RNA that can be used to detect, by hybridization or complementary base-pairing, a target nucleic acid sequence which is homologous or complementary.

restriction site: A nucleotide sequence, usually 4 to 6 base pairs long, which is recognized and susceptible to cleavage in a specific fashion by a restriction enzyme.

sequence: two or more DNA or RNA nucleotides in a given order.

stringency: refers to the conditions under which hybridization takes place. At high stringency only exact matches of DNA and RNA will hybridize stably. Under low stringency, 80-90% homologous sequences may still hybridize.

BIOLOGICAL MATERIALS AND REAGENTS

Bacteria

E. coli = *Escherichia coli*
T. bry = *Treponema bryantii*
T. hyo = *Treponema hyodysenteriae*
T. innocens = *Treponema innocens*
T. succ = *Treponema succinifaciens*

Buffers and Media

BHIS medium: dehydrated brain heart infusion, 3.7 g; L-cysteine-HCl, 0.1 g.; resazurin (0.1%), 0.1 ml; distilled water, 87 ml. Adjust pH to 7.3, then heat (<100° C.) until the resazurin indicator becomes colorless. Dispense in anaerobic culture tubes (18 × 142 mm) under a nitrogen atmosphere; 6.3 ml per tube. Autoclave, cool, add 0.7 ml fetal calf serum (heat inactivated), and "Teflon"-coated stir bar (3 × 10 mm), and flush with sterile, oxygen-free N$_2$ until the resazurin (resorfin) indicator becomes colorless. Add 0.1 ml of spirochete culture, close tube with a neoprene rubber stopper, seal with plastic tape, and inject 1.0 ml sterile air through the stopper to yield an atmosphere of about 1% O$_2$. Incubate at 39° C. on a magnetic stirring platform.

HP4 buffer: distilled water, 66.75 ml; SSC (20X), 20 ml; 0.25M NaPO$_4$ (pH 6.8), 10 ml; 200 mM EDTA (disodium), 0.5 ml; Salmon testes DNA (10 mg/ml) (sonicated and denatured), 0.25 ml; 50X Denhardt's solution, 2 ml; SDS (20%), 0.5 ml.

HP1buffer: Same as HP4 buffer except distilled water is 81.75 ml and SSC (20X) is 5 ml.

RFG medium: T. B. Stanton and E. Canale-Parola, Arch. Microbiol. 127: 145-156 (1980), incorporated herein by reference.

RTY medium: W. M. Cwyk and E. Canale-Parola, Arch. Microbiol. 122: 231-239 (1979), incorporated herein by reference.

SSC (20 X): saline sodium citrate-NaCl, 175.3 g; sodium citrate, 88.2 g; distilled water, 1000 ml; pH to 7.0 [as described in T. Maniatis et al., "Molecular Cloning: A Laboratory Manual," Cold Spring Harbor Laboratory, Cold Spring Harbor, NY (1982)].

SSC (10X): SSC (20X), 50 ml; distilled water, 50 ml.
SSC (4X): SSC (20X), 20 ml; distilled water, 80 ml.
SSC (2X): SSC (20X), 10 ml; distilled water, 90 ml.

T4 polynucleotide kinase buffer (10X): 0.5M Tris-HCl (pH 7.6), 0.1M MgCl$_2$, 50 mM dithiothreitol, 1 mM spermidine HCl, 1 mM EDTA (pH 8.0) [as described in Maniatis, supra].

TE buffer: Tris-EDTA buffer-10 mM Tris-HCl, 1 mM EDTA, pH 8.0 [as described in Maniatis, supra].

TBS: Tris-buffered saline - 10 mM Tris-HCl, 150 mM NaCl, pH 7.4.

| Restriction Enzyme | Cleavage Site |
|---|---|
| HindIII | 5' ... A AGCTT ... 3' |
| HinfI | 5' ... G ANTC ... 3' |
| SspI | 5' ... AAT ATT ... 3' |

DETAILED DESCRIPTION OF THE INVENTION

In preparation for developing oligonucleotide probes for *T. hyo*, we determined partial nucleotide sequences of the 16S rRNA molecule of *T. hyo* strains B204, B78, and A-1, *T. innocens* strains B256 and 4/71, *T. suc-*

*cinifaciens* strain 6091, and *T. bryantii* strain RUS-1. Upon comparison of these sequences, regions of the *T. hyo* 16S rRNA molecule that differed from analogous regions of the other treponemes were identified. One such region which was homologous across all the strains within each species was selected. This region is represented by the ss-rRNA sequences shown in the appended Sequence Listing for *T. hyo, T. innocens, T. succinifaciens, T. bryantii,* and *E. coli* as SEQ ID NOS. 1-5, respectively. The *E. coli* sequence is used to identify the bases homologous to the *T. hyo-T. innocens* mismatches, using the numbering system employed by Noller [Ann. Rev. Biochem. 53: 131 (1984)]. These mismatches are bases 629 and 647.

A strategy for constructing a probe within the scope of the invention is initiated by predetermining the probe's length. It is envisioned that probes useful herein would range in size from about 15 to 50 bases, with the preferred size being about 17 to 35 bases. A sequence of the predetermined length, occurring within the *T. hyo* rRNA and including at least one of the two base mismatches with *T. innocens*, is then selected. The nucleotide sequence complementary to the selected rRNA sequence is thereafter determined, and the oligodeoxyribonucleotide or oligoribonucleotide probe is synthesized as the inverse of the complementary sequence. In this way, the probe is in correct orientation for binding to native rRNA in samples to be assayed.

Given below in the Sequence Listing as SEQ ID NO. 6 is the base sequence corresponding to the inverse of the complement of the *T. hyo* rRNA extending 49 bases to either side of the 629 and 647 mismatch sequences. The sequences of probes encompassed by the invention can be ascertained directly from SEQ ID NO. 6.

Under stringent conditions, probes of the invention will bind to *T. hyo* rRNA but not to the rRNA of other treponemes or *Escherichia coli*. This specificity makes these probes useful for the detection of *T. hyo* in complex samples such as fecal material. This approach has several advantages over cloned genomic DNA probes. Increased sensitivity is obtained because the target of the probe, rRNA, is present in up to 10,000 copies per cell as opposed to only 1-10 gene copies per cell. Also short oligonucleotide probes can be used which reduce the hybridization time from 12-24 hrs to 2 hrs. This results in a highly sensitive and specific test that can be completed in 1-2 days.

In addition, these probes can be used to differentiate between strains of *T. hyo* based on RFLP analysis. DNA isolated from *T. hyo* strains are digested with restriction endonucleases, the fragments are separated by electrophoresis through an agarose gel, transferred to a solid support, and hybridized with the oligonucleotide probe. When probed in this way, strains of *T. hyo* can be differentiated based on the positions of the DNA bands that hybridize with the probe. This application is epidemiologically useful for following the transmission of *T. hyo*.

To enable detection, the probes may be bound to a radioactive, enzymatic, or organic label by any conventional procedure in the art. For instance, by leaving the 5'-OH end nonphosphorylated during construction, the probes are readily end-labelled using T4 polynucleotide kinase and $\gamma$ AT$^{32}$P as described in detail in Example 2.

The following examples are intended only to further illustrate the invention and are not intended to limit the scope of the invention which is defined by the claims.

EXAMPLE 1

Identification of *T. hyo* 16S rRNA Signature Region

The sequences of 16S rRNA molecules from three strains of *T. hyo* (B204, B78, and A-1), two strains of *T. innocens* (B256 and 4/71), and one strain each of *T. succinifaciens* (6091) and *T. byrantii* (RUS-1) were compared for variable regions. A variable region comprising two base mismatches between *T. hyo* and *T. innocens* was identified and provided the basis for constructing probes which would differentiate *T. hyo* from other *Treponema* species. The *T. hyo* rRNA sequence was also compared to that of *E. coli*.

EXAMPLE 2

Construction of 17 Base Probe

A 17-base oligodeoxynucleotide probe corresponding to bases 42 through 58 of SEQ ID NO. 6 [5'-CCA-AGA-CTT-ACA-GTA-TC-3' (SEQ ID NO. 7)] was synthesized using a commercial DNA synthesizer. The 5'-OH end was initially left nonphosphorylated to allow for subsequent 5' terminal phosphorylation with $\gamma$ AT$^{32}$P. The labelling was conducted by combining into a reaction mixture the following: $\gamma$ AT$^{32}$P (4500 Ci/mmol), 10 $\mu$l; 10X T4 polynucleotide kinase buffer, 2 $\mu$l; 17-base oligomer, 0.5 $\mu$g; T4 polynucleotide kinase (10 U/$\mu$l), 2 $\mu$l; and distilled water to 20 $\mu$l. The mixture was incubated at 37° C. for 45 min, and the reaction was stopped by addition of 2 $\mu$l of 0.5M EDTA. The volume was then brought up to 100 $\mu$l with TE buffer, and unincorporated nucleotides were removed on a 1-ml Sephadex G-25 spin column. The resultant labelled probe was stored at 4° C.

EXAMPLE 3

Construction of 28 Base Probe

A 28-base oligodeoxynucleotide probe corresponding to bases 47 through 74 of SEQ ID NO. 6 [5'-ACT-TAC-AGT-ATC-CGA-GGC-GTT-TCC-GAA-G-3' (SEQ ID NO. 8)] was synthesized using a commercial DNA synthesizer and labelled as described in Example 2.

EXAMPLE 4

Preparation of Sample Material rRNA: rRNA samples isolated from Treponema and *E. coli* cells were diluted in TE buffer to the desired concentrations (determined spectrophotometrically by absorbance at 260 nm) in a final volume of 100 $\mu$l. Samples were denatured by the addition of 3 vols. of formaldehyde/SSC (18%/10X), followed by heating at 65° C. for 15 min. Samples were cooled to room temperature before use.

Whole cells: *T. hyo* (strains B78, B204, B169, A-1, B8044, B6933, and Ack 300/8) and *T. innocens* (strains B256 and 4/71) were grown in BHIS broth under a 1% O$_2$ atmosphere at 39° C. *E. coli* strain HB101 was grown in BHIS broth aerobically. *T. succinifaciens* strain 6091 was grown in RTY medium and *T. bryantii* strain RUS-1 was grown in RFG medium. When cell populations in BHIS broth cultures reached densities of 1-5×10$^8$ cells per ml, as determined by counting in a Petroff-Hauser counting chamber, cells were collected by centrifugation (3000×g, 15 min) and resuspended in TBS buffer to a final density of 10$^8$ cells per ml. Cells were aliquoted into Eppendorf tubes and frozen at −80° C. until use. When needed, stocks were thawed and dilutions of cells were made in TBS.

Feces: Thirteen pigs were used for experiments involving inoculation with *T. hyo*. Feed was withheld from pigs for 24 hrs prior to first inoculation. Pigs were inoculated twice, 24 hrs apart, with 100 ml of *T. hyo* in BHIS medium ($10^9$ cells per ml) and were returned to normal feeding schedule 1 hr after the second inoculation. Pigs were screened for the development of swine dysentery by microscopic examination of fecal samples for the presence of spirochetes morphologically similar to *T. hyo* and by plating fecal samples onto blood agar plates containing spectinomycin. Visual examination of fecal consistency and general appearance of the pigs were also taken into account. Fecal samples, both from healthy pigs (3–6 wks old) and from pigs experimentally inoculated with *T. hyo*, were taken from the pig's rectum using cotton swabs. Swabs were placed in 3-ml sterile, anaerobic trypticase soy broth on ice, and vortexed to suspend the fecal material. A 1.5-ml portion of the suspension was placed in a microfuge tube, centrifuged ($12,400 \times g$, 15 min), and 1.35 ml of supernatant was removed and discarded. Pellets were resuspended in the remaining liquid and stored at 4° C. or −20° C. until use. Dilutions of the thawed suspensions were made in TBS buffer.

Hybridization Procedures for Examples 5–11

Slot blot preparation of membranes and sample application: All samples were applied to nylon membranes (Hybond N, Ambersham Corp., Chicago, IL) using a Manifold II slot blot apparatus (Schleicher and Schuell, Keene, NH). This was accomplished by first soaking two pieces of filter paper in 10X SSC and placing them at the base of the slot blot unit. The membrane, pretreated with distilled water and 10X SSC, was placed on the wet filter papers, and the unit was assembled. A vacuum source was attached, and each slot to be used was washed with 500 µl 10X SSC. Samples to be probed (prepared as described above, ≦500 µl) were dispensed into the appropriate slots, allowed to be pulled onto the membrane by vacuum, then washed with 500 µl 10X SSC. After the SSC had been drawn through the well, the vacuum was released and the slot blot apparatus was disassembled. The membrane was dried at 37° C. for 20 min, then heated at 80° C. for 2 hrs to bind the samples to the membrane.

Hybridization and development: Nylon membranes were prehybridized for 2–4 hrs in heat-sealable plastic bags containing HP1 (for 17-base probe) or HPH4 (for 28-base probe) buffer. The prehybridization and hybridization temperatures employed for each of the 17-base probe and the 28-base probe under low and high stringency and sensitivity conditions are summarized in Table I below.

TABLE I

| Probe (bp) | Temperature (°C.) Stringency | |
|---|---|---|
| | Low | High |
| 17 | 40 | 45 |
| 28 | 65 | 71 |

After prehybridization, the HP1/HP4 buffer was poured off, and fresh HP1/HP4 buffer containing $^{32}$P-labelled probe ($1-2 \times 10^6$ cpm) was added. Hybridization was carried out overnight. Next the membranes were removed from the bags and washed twice in 2X SSC/0.1% SDS for 1 min each at room temperature, then once in 2X SSC/0.1% SDS for 20 min at room temperature. After washing, the membrane was placed between two pieces of plastic wrap and exposed to X-ray film (Kodak "X-OMAT" film, Eastman Kodak, Rochester, NY) using an intensifying screen at −80° C. for times ranging from overnight to 2 days. Bands were visualized by developing the film.

EXAMPLE 5

Results of hybridizing 17-base probe with rRNA, low stringency: The 17-base oligodeoxynucleotide probe of Example 2 was tested for its ability to hybridize with rRNA prepared as in Example 4 from different treponemes and *E. coli*. Under hybridization conditions of low stringency, where the probe should bind to both complementary sequences and to sequences with a 1-base difference (i.e., *T. innocens*), *T. hyo* (strains B78, B204, and A-1) and *T. innocens* (strains B256 and 4/71) rRNA bound the probe strongly at concentrations down to 10 ng. However, *T. succinifaciens*, *T. bryantii*, and *E. coli*, with 5- or 6-base differences, did not bind the probe.

EXAMPLE 6

Results of hybridizing 17-base probe with rRNA, high stringency: When hybridized under high stringency conditions, the 17-base probe of Example 2 continued to bind *T. hyo* rRNA at concentrations as low as 10–25 ng, but 750 ng of *T. innocens* rRNA was required to detect any binding of the probe. Thus, the DNA probe was 10–50 times more sensitive for *T. hyo* rRNA than for *T. innocens* rRNA under high-stringency conditions.

EXAMPLE 7

Results of hybridizing 17-base probe with whole cells, high stringency: The 17-base probe demonstrated the same specificity toward whole cells as toward rRNA and was also highly sensitive. *T. hyo* (strains B204 and B78) could be detected at dilutions down to $1-2.5 \times 10^4$ cells; however, the detection threshhold for *T. innocens* (strain 4/71) was $5 \times 10^5$ cells.

EXAMPLE 8

Results of hybridizing 17-base probe with fecal samples, high stringency: Two samples from pigs exhibiting clinical signs of swine dysentery, and one sample from a healthy control pig, were bound to a nylon membrane and hybridized with the 17-base DNA probe. The probe hybridized strongly with the samples from dysenteric pigs but only bound very weakly to the control sample.

EXAMPLE 9

Results of hybridizing 28-base probe with rRNA, high stringency: The 28-base probe of Example 3 (SEQ ID NO. 8) was tested for its ability to hybridize with rRNA prepared as in Example 4 from different treponemes and *E. coli*. Under hybridization conditions of high stringency, the probe bound strongly to rRNA from all three strains of *T. hyo* tested (B78, B204, and A-1) at concentrations down to 1 ng. No binding was observed by rRNA from *T. innocens* (strains B256 and 4/71), *T. succinifaciens* (strain 6091), *T. bryantii* (strain RUS-1), or *E. coli* (strain HB101) at 50 ng, the highest level tested.

EXAMPLE 10

Results of hybridizing 28-base probe with whole cells, high stringency: The 28-base probe of Example 3 was tested for its ability to hybridize with whole cells prepared as in Example 4 from different treponemes. Under hybridization conditions of high stringency, the probed bound strongly to cells from seven strains of *T. hyo* tested (B78, B204, B169, A-1, B8044, 56933, and ACK 300/8) at dilutions down to $2.5 \times 10^3$ cells. For *T. innocens* (strains B256 and 4/71), the probe failed to detect cells at dilutions as high as $10^5$.

EXAMPLE 11

Results of hybridizing 28-base probe with fecal samples, high stringency: The 28-base probe of Example 3 was tested for its ability to detect *T. hyo* in fecal samples. This trial was conducted essentially as described in Example 8, using nine inoculated pigs and one uninoculated pig as a negative control. Three pigs developed clinical signs of swine dysentery. *T. hyo* was detected in fecal samples from those pigs. However, the organism was not detected in the remaining animals.

EXAMPLE 12

17-Base Probe in RFLP Assay for Distinguishing Strains of *T. hyo*: DNA from *T. hyo* (strains B78, B204, B169, and A-1) was isolated by cesium chloride gradient centrifugation. A 500-ml culture of *T. hyo* grown in BHIS medium was centrifuged ($3000 \times g$, 15 min). Cells were resuspended in TBS buffer and centrifuged again. To the cell pellet 1.6 ml TE buffer was added, and the cells were resuspended. Next 0.4 ml lysozyme (10 mg/ml in TE buffer) was added, sample was placed on ice for 15 min, then 50 μl proteinase K (5 mg/ml in distilled $H_2O$) and 0.4 ml 0.5M EDTA (pH 8.0) were added. After mixing, 0.2 ml sodium N-laurylsarcosine (10% solution in distilled $H_2O$) was added, the sample was mixed gently but thoroughly and incubated at 65° C. overnight. Solid CsCl was added to a final concentration of 1.0 g CsCl/1.0 ml lysed cell suspension. Solution was mixed gently until CsCl went into solution.

CsCl/lysed cell suspension was transferred to a polyallomer tube, sealed, and run in a Vti 65 rotor at 65,000 rpm for 4 hrs. DNA was collected through the side of the tube with a 16-gauge needle and dialyzed extensively against TE buffer to remove the CsCl from the sample. Samples were stored at 4° C. until use.

Each DNA sample was cut with a restriction endonuclease following the suppliers protocols. Digested DNA was run in a 1% agarose gel with TBE running buffer, stained with ethidium bromide, denatured, renatured, and transferred to nylon by southern transfer using standard procedures (as described in Maniatis, 1982, supra).

The nylon membrane was dried at 37° C. for 20 min, then heated at 80° C. for 2 hrs to bind the DNA to the membrane. The membrane was placed in a heat-sealable plastic bag and prehybridized in HP4 buffer (15 ml/$20 \times 20$ cm membrane) at 37° C. for 2 hrs. The HP4 buffer was poured off, and HP4 buffer containing $^{32}P$-labelled probe ($5-7 \times 10^6$ cpm) was added and hybridization was carried out at 37° C. for 3 hrs. The membrane was removed from the bag and washed twice in 4X SSC/0.1% SDS (250 ml) at room temperature, then twice in the same buffer (250 ml) at 37° C. for 30 min. This low-stringency wash was used to maximize the number of DNA fragments bound by the probe. Film was exposed to the membrane for 2 days, then developed.

Depending on the restriction endonuclease used, 1–4 bands were detected. Restriction endonucleases HindIII, HinfI, and SspI were best for finding differences between *T. hyo* strains. With this method *T. hyo* strains B204, B78, and B169 were easily distinguished from one another.

It is understood that the foregoing detailed description is given merely by way of illustration and that modification and variations may be made therein without departing from the spirit and scope of the invention.

Sequence Listing

| SEQ ID NO. | rRNA Source | SS-rRNA Sequence (5' .... 3') |
|---|---|---|
| 1 | *T. hyo* (3)[1] | C U U C G G A A A C  G C C U C G G A U A  C U G U A A G U C U  U G G |
| 2 | *T. innocens* (2)[2] | C U U C G G G[3] A A C  G C C U C G G A U A  C U G U G A G U C U  U G G |
| 3 | *T. succ* | C C C C G N[4] A A C C  G C G C U G G G A A  C U G C U G G G C U  U G A |
| 4 | *T. bryantii* | C C C C G N A A C U  G C G U U G G A A A  C U G C A G A A C U  U G A |
| 5 | *E. coli* | C C U G G G A A C U  G C A U C U G A U A  C U G G C A A G C U  U G A |
|   |   |             629[5]                                                 647 |

[1] *T. hyodysenteriae* strains B78, B204, and A-1.
[2] *T. innocens* strains B256 and 4/71.
[3] X; base which differs from the sequence of *T. hyodysenteriae*.
[4] N; variable nucleotide.
[5] Base numbers from "Structure of Ribosomal RNA" [Harry F. Noller, Ann. Rev. Biochem. 53: 119–162 (1984), see page 131].

Sequence Listing

| SEQ ID NO. | Probe Sequence[1] |
|---|---|
| 6 | TTCCACCGCT  ACACCNNGAA  TTCCATCATC  CCCTACAATA<br>TCCAAGACTT[2]  ACAGTATCCG  AGGCGTTT[3]CC  GAAGTTGAGC<br>TTCGGTCTTT  CACCTTAGAC  TTATAAGTCC  GCCTACT |
| 7 | CCAAGACTT[2]A  CAGTATC |
| 8 | ACTT[2]ACAGTA  TCCGAGGCGT  TT[3]CCGAAG |

[1] DNA probes are represented; for RNA probes, U's would be substituted for T's.
[2] Complementary to mismatch 647 in *T. hyo* rRNA, SEQ ID NO. 1.
[3] Complementary to mismatch 629 in *T. hyo* rRNA, SEQ ID NO. 1.

We claim:

1. A labelled, single-stranded oligonucleotide probe having a base sequence corresponding to SEQ ID NO. 6, having a length of about 15-50 bases and including at least one of the bases at positions 50 and 68 in said SEQ ID NO. 6.

2. A single-stranded oligonucleotide probe as described in claim 1, wherein said length is 17-35 bases.

3. A single-stranded oligonucleotide probe as described in claim 2 and including only one of said bases at positions 50 and 68.

4. A single-stranded oligonucleotide probe as described in claim 2 and including both of said bases at positions 50 and 68.

5. A single-stranded DNA probe as described in claim 1 and corresponding to the 17-base sequence of SEQ ID NO. 7.

6. A single-stranded DNA probe as described in claim 1 and corresponding to the 28-base sequence of SEQ ID NO. 8.

7. A method for detecting *Treponema hyodysenteriae* in a biological material sample comprising contacting said sample with a labelled, single-stranded oligonucleotide probe having a length of about 15-50 bases, wherein the base sequence of said probe corresponds to a sequence encompassed by SEQ ID NO. 6 and including at least one of the bases at positions 50 and 68 in said SEQ ID NO. 6, and wherein the contacting is under conditions by which said probe will bind to complementary ribosomal RNA of the *Treponema hyodysenteriae* to form a hybridization product, and identifying said hybridization product.

8. A method as described in claim 7 wherein said biological material sample is fecal material.

9. A method as described in claim 8 wherein said biological material is selected from the group consisting of isolated whole cells of *Treponema hyodysenteriae* and isolated ribosomal RNA of *Treponema hyodysenteriae*.

10. A method as described in claim 7, wherein the length of the probe is 17-35 bases and includes only one of said bases at positions 50 and 68.

11. A method as described in claim 7, wherein the length of the probe is 17-35 bases and includes both of said bases at positions 50 and 68.

12. A method as described in claim 7, wherein the probe is a DNA probe and corresponds to the 17-base sequence of SEQ ID NO. 7.

13. A method as described in claim 7, wherein the probe is a DNA probe and corresponds to the 28-base sequence of SEQ ID NO. 8.

14. A method for identifying a strain of *Treponema hyodysenteriae* comprising:
   a. digesting DNA of said strain with one or more restriction enzymes to produce DNA fragments of various sizes;
   b. contacting said DNA fragments with a labelled, single-stranded oligonucleotide probe having a length of about 15-50 bases, wherein the base sequence of said probe corresponds to a sequence encompassed by SEQ ID NO. 6 and including at least one of the bases at positions 50 and 68 in said SEQ ID NO. 6, and wherein the contacting is under conditions by which said probe will hybridize with those of the DNA fragments which are complementary to the probe; and
   c. identifying the distribution of the hybridized fragment sizes resulting from step (b).

15. A method as described in claim 14, wherein the length of the probe is 17-35 bases and includes only one of said bases at positions 50 and 68.

16. A method as described in claim 14, wherein the length of the probe is 17-35 bases and includes both of said bases at positions 50 and 68.

17. A method as described in claim 14, wherein the probe is a DNA probe and corresponds to the 17-base sequence of SEQ ID NO. 7.

18. A method as described in claim 14, wherein the probe is a DNA probe and corresponds to the 28-base sequence of SEQ ID NO. 8.

* * * * *